United States Patent
Stössel et al.

(10) Patent No.: US 7,423,151 B2
(45) Date of Patent: *Sep. 9, 2008

(54) METHOD FOR THE PRODUCTION OF HIGHLY PURE TRIS-ORTHO-METALATED ORGANO-IRIDIUM COMPOUNDS

(75) Inventors: Philipp Stössel, Frankfurt (DE); Hubert Spreitzer, Viernheim (DE); Heinrich Becker, Hofheim (DE)

(73) Assignee: Merck Patent GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/483,359

(22) Filed: Jul. 7, 2006

(65) Prior Publication Data

US 2006/0252936 A1   Nov. 9, 2006

Related U.S. Application Data

(63) Continuation of application No. 10/470,811, filed as application No. PCT/EP02/00920 on Jan. 30, 2002, now Pat. No. 7,084,273.

(30) Foreign Application Priority Data

Feb. 1, 2001 (DE) ................... 101 04 426

(51) Int. Cl.
  *C07F 15/00* (2006.01)
  *B01J 31/02* (2006.01)
(52) U.S. Cl. ................. 546/4; 502/152; 546/2
(58) Field of Classification Search .......... 546/2, 546/4; 502/152
  See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 6,821,645 B2 * | 11/2004 | Igarashi et al. | 428/690 |
| 7,084,273 B2 * | 8/2006 | Stossel et al. | 546/4 |
| 7,125,998 B2 * | 10/2006 | Stossel et al. | 546/4 |

FOREIGN PATENT DOCUMENTS

| | | |
|---|---|---|
| EP | 1 138 746 | 10/2001 |
| EP | 1 175 128 | 1/2002 |
| JP | 2001357977 | 12/2001 |
| JP | 2002/105055 | 4/2002 |
| WO | WO 00-70655 | 11/2000 |
| WO | WO-01/41512 | 6/2001 |
| WO | WO-02/02714 | 1/2002 |
| WO | WO-02/15645 | 2/2002 |

OTHER PUBLICATIONS

King et al., "Excited-State Properties of a Triply Ortho-Metalated Iridium(III) Complex," *J. Am. Chem. Soc.*, vol. 107, pp. 1431-1432 (1985).
Dedeian et al., "A New Synthetic Route to the Preparation of a Series of Strong Photoreducing Agents: *fac* Tris-Ortho-Metalated Complexes of Iridium (III) with Substituted 2-Phenylpyridines," *Inorg. Chem.*, vol. 30, pp. 1685-1687 (1991).
Garces et al., "Structures of *ortho*-Metalated [2-(*p*-Tolyl)pyridine]iridium(III) Coomplexes," *Acta Cryst.*, C49, pp. 1117-1120 (1993).
Colombo et al., "Facial Tris Cyclometalated Rh3+ and Ir3+ Complexes: Their Synthesis, Structure, and Optical Spectroscopic Properties," *Inorg. Chem.*, vol. 33, pp. 545-550 (1994).
Djurovich et al., "Ir(III) Cyclometalated Complexes As Efficient Phosphorescent Emitters In Polymer Blend And Organic LEDs," *Polymer Reprints*, vol. 41 (1), pp. 770-771 (2000).

* cited by examiner

*Primary Examiner*—Charanjit S Aulakh
(74) *Attorney, Agent, or Firm*—Connolly Bove Lodge & Hutz LLP

(57) ABSTRACT

The present invention relates to a process for preparing highly pure tris-ortho-metallated organoiridium compounds and such pure organometallic compounds, especially compounds of the $d^8$ metals, which may find use as coloring components in the near future, as active components (=functional materials) in a series of different types of application which can be classed within the electronic industry in the broadest sense.

15 Claims, No Drawings

METHOD FOR THE PRODUCTION OF HIGHLY PURE TRIS-ORTHO-METALATED ORGANO-IRIDIUM COMPOUNDS

This application is a continuation of Ser. No. 10/470,811, filed Nov. 24, 2003 now U.S. Pat. No. 7,084,273,which is a 371 of PCT/EP02/00920, filed Jan. 30, 2002, which claims benefit to German Application No. 101 04426.7, filed Feb. 1, 2001.

Organometallic compounds, especially compounds of the $d^8$ metals, will find use in the near future as coloring components, as active components (=functional materials) in a series of different types of application which can be classed within the electronics industry in the broadest sense.

The organic electroluminescent devices based on purely organic components (for a general description of the construction, see U.S. Pat. Nos. 4,539,507 and 5,151,629) and their individual components, the organic light-emitting diodes (OLEDs), have already been introduced onto the market, as confirmed by the car radios having organic displays from Pioneer. Further products of this type will shortly be introduced. In spite of this, distinct improvements are still necessary here, in order to provide real competition to the currently market-leading liquid crystal displays (LCDs) or to overtake these.

A development in this direction which has emerged in the last two years is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4-6].

For theoretical reasons relating to the spin probability, up to four times the energy efficiency and performance efficiency are possible using organometallic compounds. Whether this new development will establish itself firstly depends strongly upon whether corresponding device compositions can be found which can also utilize these advantages (triplet emission=phosphorescence compared to singlet emission=fluorescence) in OLEDs. The essential conditions for practical use are in particular a long operative lifetime, a high stability against thermal stress and a low use and operating voltage, in order to enable mobile applications.

Firstly, there has to be efficient chemical access to the corresponding, highly pure organoiridium compounds. Especially taking into account the cost of iridium, this is of decisive importance for the economic utilization of the compound class specified.

The literature describes a plurality of processes for preparing tris-ortho-metallated organoiridium compounds. The general access routes, the yields achieved by them and their disadvantages are detailed briefly hereinbelow using the basic structure of the compound class specified, fac-tris[2-(2-pyridinyl-κN)phenyl-κC]-iridium(III).

Starting from hydrated iridium(III) chloride and 2-phenylpyridine, fac-tris[2-(2-pyridinyl-κN)phenyl-κC]-iridium (III) was obtained after laborious chromatographic purification methods in about a 10% yield [K. A. King, P. J. Spellane, R. J. Watts, J. Am. Chem. Soc., 1985, 107, 1431-1432].

K. Dedeian et al. describes a process starting from iridium (III) acetylacetonate and 2-phenylpyridine which provided fac-tris[2-(2-pyridinyl-κN)phenyl-κC]-iridium(III) in a 45% yield. Similarly to the abovementioned process, the product in this process also has to be freed from impurities by chromatographic methods, and halogenated hydrocarbons are used here, as a consequence of their solubility behaviour. [K. Dedeian, P. I. Djurovich, F. O. Garces, G. Carlson, R. J. Watts Inorg. Chem., 1991, 30, 1685-1687].

In a third literature process, di-μ-chlorotetrakis[2-(2-pyridinyl-κN)phenyl-κC]di-iridium(III) is used as a reactant and initially has to be prepared in an approx. 72% yield from hydrated iridium(III) chloride and 2-phenylpyridine [S. Spouse, K. A. King, P. J. Spellane, R. J. Watts J. Am. Chem. Soc., 1984, 106, 6647]. This is then reacted with 2-phenylpyridine and double molar amounts of silver trifluoromethanesulfonates, based on the di-μ-chlorotetrakis[2-(2-pyridinyl-κN)phenyl-κC]di-iridium(III). After chromatographic purification, the authors obtain tris[2-(2-pyridinyl-κN)phenyl-κC]-iridium(III) in a 75% yield [M. G. Colombo, T. C. Brunold, T. Riedener, H. U. Gudel Inorg. Chem., 1994, 33, 545-550]. In addition to the chromatographic purification which is again effected with the aid of the halogenated hydrocarbons, the use of double molar amounts of silver trifluoromethanesulfonate based on di-μ-chlorotetrakis[2-(2-pyridinyl-κN)phenyl-κC]di-iridium(III) is disadvantageous.

In the table below, these references are compared for a better overview, including the comparative experiment carried out in Example 1.

TABLE 1

Literature comparison of existing preparation processes

| | Reference 1 | Reference 2 Literature | Reference 2 Comparative exp. | Reference 3 |
|---|---|---|---|---|
| Reactants | IrCl$_3$<br>2-phenylpyridine | Ir(acac)$_3$<br>2-phenylpyridine | Ir(acac)$_3$<br>2-phenylpyridine | [Ir(ppy)$_2$Cl]$_2$<br>2-phenylpyridine<br>AgO$_3$SCF$_3$ |
| Solvent | 2-ethoxyethanol/water | ethylene glycol | ethylene glycol | none |
| Temperature | — | 196°-198° C. | 196°-198° C. | 110° C. |
| Concentration of iridium reactant | 0.03 mol/l | 0.02 mol/l | 0.02 mol/l | — |
| Molar ratio of iridium reactant to 2-phenylpyridine | 1:4 | 1:6.3 | 1:6.3 | 1:15 |
| Reaction time | 24 h | 10 h | 10 h | 24 h |

TABLE 1-continued

Literature comparison of existing preparation processes

|  | Reference 1 | Reference 2 Literature | Comparative exp. | Reference 3 |
| --- | --- | --- | --- | --- |
| Yield | approx. 10% of [Ir(μ-Cl)(ppy)]$_2$ as a by-product | 45% | 39.3-44.0% | 75% |
| Purity by HPLC | no data | no data | 94.0-96.0% | no data |

Reference 1: K. A. King, P. J. Spellane, R. J. Watts, J. Am. Chem. Soc., 1985, 107, 1431-1432. S. Spouse, K. A. King, P. J. Spellane, R. J. Watts, J. Am. Chem. Soc., 1984, 106, 6647-6653.
Reference 2: K. Dedeian, P. I. Djurovich, F. O. Garces, G. Carlson, R. J. Watts Inorg. Chem., 1991, 30, 1685-1687.
Reference 3: M. G. Colombo, T. C. Brunold, T. Riedener, H. U. Güdel Inorg. Chem., 1994, 33, 545-550.

It has now been found that, surprisingly, compounds I (according to Scheme 1) are obtained reproducibly in a yield of from about 90 to 95%, without using chromatographic purification methods, in purities of >99.9% by HPLC, starting from iridium(III) acetylacetonate or similar 1,3-diketo chelate complexes and 2-arylpyridines with suitable choice of the reaction parameters such as reaction temperature, concentrations and reaction times (see method A, examples 2 to 5).

The present invention provides a process for preparing compounds I

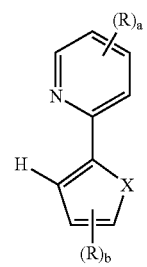

where
X is —CH═CH—, —CR═CH—, —CR═CR—, N—H, N—R$^1$, O, S or Se; preferably —CH═CH—, —CR═CH— or S;
R is the same or different at each occurrence and is F, Cl, Br, NO$_2$, CN, a straight-chain or branched or cyclic alkyl or alkoxy group having from 1 to 20 carbon atoms, in each of which one or more nonadjacent CH$_2$ groups may be replaced by —O—, —S—, —NR$^1$—, or —CONR$^2$—, and in each of which one or more hydrogen atoms may be replaced by F, or an aryl or heteroaryl group having from 4 to 14 carbon atoms which may be substituted by one or more nonaromatic radicals R; and a plurality of substituents R, either on the same ring or on the two different rings, may in turn together form a further mono- or polycyclic ring system;
R$^1$ and R$^2$ are the same or different and are each H or an aliphatic or aromatic hydrocarbon radical having from 1 to 20 carbon atoms,
a is 0, 1, 2, 3 or 4, preferably 0 or 1,
b is 0, 1 or 2, preferably 0 or 1, by reacting a compound of the formula (Ia)

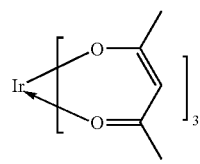

with a compound of the formula (Ib)

(Ib)

where the radicals X, R, a and b are each as defined in the formula (I) in a dipolar protic solvent, an etherified derivative derived therefrom or N-methylpyrrolidinone (NMP), at temperatures in the range from 160 to 220° C. and a concentration of the iridium reactant (based on iridium) in the range from 0.05 to 1.00 mol/l, the concentration of the ligand used (arylpyridyl derivative) being a factor of from 4 to 20 higher than that of the iridium reactant, for a period of from 20 to 100 hours.

The process according to the invention is illustrated by Scheme 1.

Scheme 1:

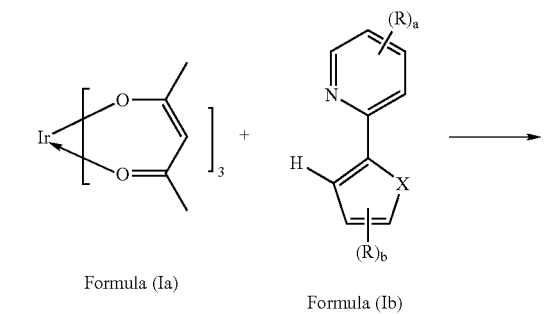

Formula (Ia)          Formula (Ib)

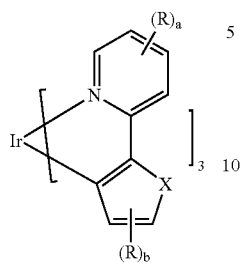

Formula (I)

Reaction media according to the invention are high-boiling, dipolar, protic solvents such as ethylene glycol or propylene glycol, or else higher diols or polyalcohols, for example glycerol, or else polyether alcohols such as polyethylene glycols, for example PEG600 and PEG1000, and also their etherified analogs, for example triethylene glycol dimethyl ether or poly(ethylene glycol) dimethyl ether, and also NMP.

According to the invention, the reaction is carried out within a temperature range of from 160° C. to 220° C., preferably in the range from 180° C. to 210° C.

According to the invention, the concentration of the iridium reactant, iridium(III) acetylacetonate or a similar 1,3-diketo chelate complex, is in the range from 0.05 to 1.00 molar, preferably in the range from 0.08 to 0.25 molar.

The molar ratio according to the invention of the iridium reactant, iridium(III) acetylacetonate or a similar 1,3-diketo chelate complex, to the aryl-pyridyl derivative is from 1:4 to 1:20, and preference is given to a ratio of from 1:6 to 1:15, particular preference to a ratio of from 1:8 to 1:12.

The preferred concentration of the aryl-pyridyl derivative is in the range from 0.50 to 10.00 molar, more preferably in the range from 0.80 to 2.50 molar.

When the concentrations are below those specified above, this leads, in addition to lower conversion, to the formation of brown by-products and therefore to the contamination of the product.

According to the invention, the reaction is carried out within from 20 to 100 h, preferably in the range from 30 to 80 h. When the reaction time is shorter than that specified, this has the consequence of an incomplete conversion of the iridium reactant used, iridium(III) acetylacetonate or a similar 1,3-diketo chelate complex, which leads to yield losses and to contamination of the product with iridium(III) acetylacetonate with a similar 1,3-diketo chelate complex.

In addition, it has been found that, surprisingly, compounds of the formula (II) are obtained reproducibly in a yield of from about 85 to 92% without using chromatographic purification methods, in purities of >99.9% by HPLC, starting from iridium(III) compounds and 2'-lithio-2-arylpyridines generated in situ in a salt metathesis reaction at low temperatures (see Scheme 2; method B, examples 6 to 8).

The present invention further provides a process for preparing compounds (II)

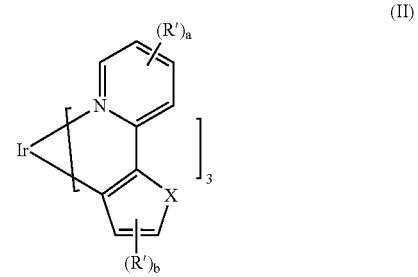

where
X is —CH=CH—, —CR=CH—, —CR=CR—, N—H, N—R$^1$, O, S or Se; preferably —CH=CH—, —CR=CH— or S;
R' is the same or different at each [lacuna] and is F, a straight-chain or branched or cyclic alkyl group having from 1 to 20 carbon atoms, in which one or more hydrogen atoms may be replaced by F, or an aryl group having from 6 to 14 carbon atoms which may be substituted by one or more nonaromatic radicals R'; and a plurality of substituents R', either on the same ring or on the two different rings, may in turn together form a further mono- or polycyclic ring system;
R$^1$ is in each case the same or different and is an aliphatic or aromatic hydrocarbon radical having from 1 to 20 carbon atoms,
a is 0, 1, 2, 3 or 4, preferably 0 or 1,
b is 0, 1 or 2, preferably 0 or 1,
by reacting a compound of the formula (IIb)

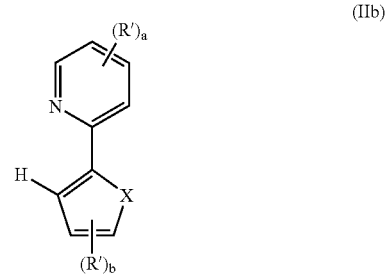

where the radicals X, R', a and b are as defined above with an organometallic lithium compound to give a compound of the formula (IIc)

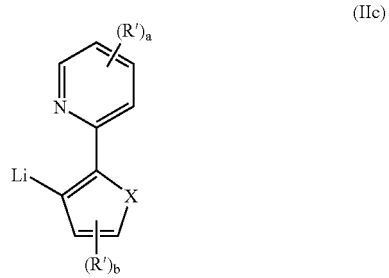

and subsequently reacting the compound of the formula (IIc) with an Ir(III) compound at low temperatures to give the target compound of the formula (II).

According to the invention, the Ir(III) compound used is an iridium(III) halide or pseudohalide such as cyanides, thiocyanates and cyanates or complexes derived therefrom, preferably iridium(III) chloride, tris(pyridine)iridium(III) chloride and tris(tetrahydrothiophene)iridium(III) chloride.

Also in accordance with the invention is the use of a 2'-lithio-2-arylpyridyl derivative prepared in situ.

According to the invention, the reaction is carried out at low temperatures, preferably in the range from −110 to +10° C., more preferably in the range from −110 to −20° C., most preferably in the range from −90 to 40° C. From a laboratory technology point of view, the reaction at −78° C. (use of an acetone/dry ice cooling bath) proves to be advantageous.

The reaction is carried out as described hereinbelow:

The 2-arylpyridine or a similar precursor according to the following scheme 2 is initially deprotonated selectively in the 2'-position at low temperatures using lithium organyls, for example n-, sec- or tert-butyllithium (Step 1), and the addition of TMEDA (N,N,N',N'-tetramethylethylene-1,2-diamine), 2-hydroxyethyldimethylamine or analogs, activators known to those skilled in the art may be advantageous. The aryllithium species generated in this way then rules in a second step in a salt metathesis reaction with the abovementioned iridium(III) compounds (Step 2).

This compound is particularly advantageous when the substituted 2-arylpyridine used bears thermally labile groups and method A, which uses very much higher temperatures, cannot be used for this reason.

Scheme 2:

Step 1:

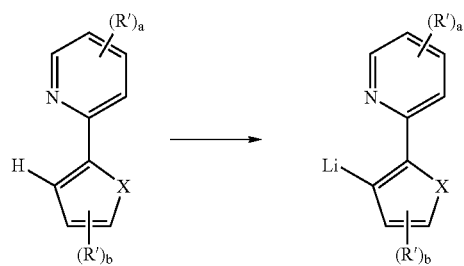

Step 2:

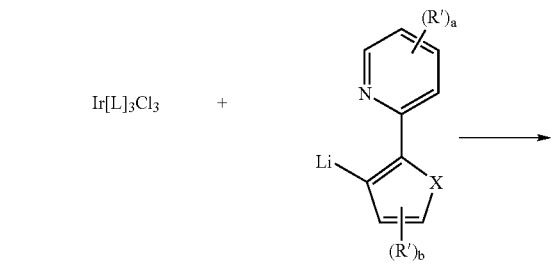

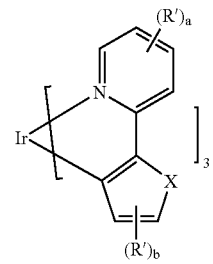

Compounds II

The symbols and indices are as already defined above for compound (II).

The compounds of the formulae (I) and (II) described in the prior art have hitherto been accessible in maximum purities of up to 96%. However, compounds of the formulae (I) and (II) can be held by the preparation according to the invention in purities of more than 99.9%, preferably of more than 99.9%. Such pure compounds were hitherto not known in the prior art and therefore likewise form part of the subject-matter of the present invention.

The present invention is illustrated in more detail by the examples which follow, without wishing to restrict it to these examples. It should now be possible for those skilled in the art in the field of organic synthesis, without any further inventive step, to carry out the reactions according to the invention on further systems as described above.

1. Synthesis of Tris-Ortho-Metallated Organoiridium Compounds:

The following syntheses were carried out up to the workup under a dry pure nitrogen atmosphere or argon atmosphere using carefully dried solvent. The reactants used were obtained from ALDRICH [1.6 molar n-butyllithium in n-hexane, ethylene glycol, triethylene glycol dimethyl ether, polyethylene glycol 600 or 1000, iridium(III) chloride, iridium(III) acetylacetonate, tris(pyridine)iridium(III) chloride] and used without further purification, or prepared by literature processes [tris(tetrahydrothiophene)iridium(III) chloride: L. Mønsted, O. Mønsted, G. Nord, K.

Simonsen Acta Chem Scand., 1993, 47, 439-443; 2-(4',5'-difluorophenyl)pyridine: similarly to E. I. Negeshi, F. T. Luo, R. Frisbee, H. Matsushita Heterocycles, 1982, 18, 117].

Method A

EXAMPLE 1 fac-Tris[2-(2-pyridinyl-κN)phenyl-κC]iridium(III)

Comparative Example according to: K. Dedeian, P. I. Djurovich, F. O. Garces, G. Carlson, R. J. Watts lnorg. Chem., 1991, 30, 1685-1687)

4.90 (10.0 mmol) of iridium(III) acetylacetonate and 9.77 g=9.0 ml (63 mmol) of 2-phenylpyridine were added to 500 ml of degassed ethylene glycol. The suspension was heated to reflux (200°-210° C. oil bath temperature) with good stirring for 10 h. After cooling to room temperature, the reaction mixture was admixed with 3000 ml of aqueous 1 N hydrochloric acid with stirring. After stirring for 5 minutes, the yellow precipitate was filtered off with suction through a glass suction filter (P3). The crude product was taken off in 2000 ml of boiling dichloromethane, and the insoluble residue was filtered off and washed twice with 200 ml of dichloromethane. The filtrate was freed of brown by-products by flash chromatography on silica gel. After adding 500 ml of methanol to the filtrate, the dichloromethane was distilled off. This resulted in a yellow, microcrystalline powder precipitating out.

The yield, at a purity of 94.0-96.0% by HPLC, was 2.57-2.88 g, corresponding to 39.3-44.0%.

EXAMPLE 2 fac-Tris[2-(2-pyridinyl-κN)phenyl-κC]iridium(III)

4.90 g (10.0 mmol) of iridium(III) acetylacetonate and 15.52 g=14.0 ml (100 mmol) of 2-phenylpyridine were added to 100 ml of degassed ethylene glycol. The suspension was heated to reflux (200-210° C. oil bath temperature) with good stirring for 16 h. After cooling to room temperature, the reaction mixture which contained the product fac-tris[2-(2-pyridinyl-κN)phenyl-κC]iridium(III) in the form of a yellow, finely crystalline precipitate was poured into 200 ml of aqueous 1 N hydrochloric acid with stirring. After stirring for 5 minutes, the mixture was filtered with suction through a glass suction filter (P3), and the yellow, finely crystalline precipitate was washed three times with 30 ml of 1 N hydrochloric acid and 5 times with 30 ml of water and subsequently dried under high vacuum at 80° for 5 h and 200° C. for 2 h.

The yield, at a purity of >99.9% by HPLC, was 6.04-6.29 g, corresponding to 92.2-96.0%.

$^1$H NMR (CDCl$_3$): [ppm]=7.84 (m, 3 H), 7.58 (m, 6 H), 7.48 (m, 3 H), 6.82 (m, 6 H), 6.69 (m, 6 H).

EXAMPLE 3 fac-Tris[2-(2-pyridinyl-κN)phenyl-κC]iridium(III)

Procedure similar to Example 2, except ethylene glycol was replaced with triethylene glycol dimethyl ether.

The yield, at a purity of >99.9% by HPLC, was 5.90-6.13 g, corresponding to 90.1-93.6%.

$^1$H NMR (CDCl$_3$): [ppm]=see Example 2

EXAMPLE 4 fac-Tris[2-(2-pyridinyl-κN)phenyl-κC]iridium(III)

A mixture of 100 g of polyethylene glycol 600 or alternatively polyethylene glycol 1000, 4.90 g (10.0 mmol) of iridium(III) acetylacetonate and 7.76 g=7.0 ml (50 mmol) of 2-phenylpyridine was melted in a Crigee apparatus and degassed by applying vacuum and back-filling with protective gas (three cycles).

The suspension was heated to 180°-200° C. with good stirring for 30 h. The acetylacetone released separated gradually in the reservoir. After cooling to 45° C., the reaction mixture which contained the product fac-tris[2-(2-pyridinyl-κN)phenylκC]iridium(III) in the form of a yellow, finely crystalline precipitate was poured into 200 ml of aqueous 1 N hydrochloric acid with stirring.

After stirring for 5 minutes, the mixture was filtered with suction through a glass suction filter (P3) and the yellow, finely crystalline precipitate was washed three times with 30 ml of aqueous 1 N hydrochloric acid and five times with 30 ml of water and subsequently dried under a high vacuum at 80° for 5 h and 200° C. for 2 h.

The yield, at a purity of >99.9% by HPLC, was 5.87-6.02 g, corresponding to 89.6-91.9%.

$^1$H NMR (CDCl$_3$): [ppm]=see Example 2

EXAMPLE 5 fac-Tris[4,5-difluoro-2-(2-pyridinyl-N)phenyl-κC] iridium(III)

4.90 g (10.0 mmol) of iridium(III) acetylacetonate and 19.12 g=(100 mmol) of 2-(4',5'-difluorophenyl)pyridine were added to 80 ml of degassed ethylene glycol. The suspension was heated to reflux (200°-210° C. oil bath temperature) with good stirring for 60 h. After cooling to room temperature, the reaction mixture which contained the product fac-tris[4,5-difluoro-2-(2-pyridinyl-κN)phenyl-κC]iridium(III) in the form of a yellow, finely crystalline precipitate was poured into 100 ml of aqueous 1 N hydrochloric acid with stirring. After stirring for 5 minutes, the mixture was filtered with suction through a glass suction filter (P3), and the yellow, finely crystalline precipitate was washed three times with 30 ml of aqueous 1 N hydrochloric acid and five times with 30 ml of water and subsequently dried in a high vacuum at 80° for 5 h and 200° C. for 2 h.

The yield, at a purity of >99.9% by HPLC, was 7.13-7.37 g, corresponding to 93.4-96.6%.

$^1$H NMR (CDCl$_3$): [ppm]=8.35 (m, 3 H), 7.66 (m, 3 H), 7.53 (m, 3 H), 6.93 (m, 3 H), 6.67 (m, 3 H), 6.39 (m, 3 H).

Method B

EXAMPLE 6 fac-Tris[2-(2-pyridinyl-κN)phenyl-κC]iridium(III)

A mixture cooled to −78° C. of 5.12 g=4.72 ml (33 mmol) of 2-phenylpyridine and 100 ml of THF was admixed with stirring over 10 min with 20.6 ml (33 mmol) of 1.6 molar n-butyllithium in n-hexane. The deep red solution was stirred at −78° C. for a further 1 h and then admixed with 2.99 g of anhydrous iridium(III) chloride.

The reaction mixture was allowed to warm to room temperature with stirring over 12 hours. Subsequently, the THF was removed on a rotary evaporator, and the yellow, semi-solid residue was suspended in 100 ml of ethanol and poured with stirring into 200 ml of aqueous 1 N hydrochloric acid. After stirring for 5 minutes, the mixture was filtered with suction through a glass suction filter (P3), and the yellow, finely crystalline precipitate was washed three times with 30 ml of aqueous 1 N hydrochloric acid and five times with 30 ml of water and subsequently dried under a high vacuum at 80° for 5 h and 200° C. for 2 h.

The yield, at a purity of >99.9% by HPLC, was 5.66-5.79 g, corresponding to 86.4-88.4%.

$^1$H NMR (CDCl$_3$): [ppm]=see Example 2.

EXAMPLE 7 fac-Tris[2-(2-pyridinyl-κN)phenyl-κC]iridium(III)

Procedure similar to Example 6, except the iridium(III) chloride was replaced with 5.36 g (10 mmol) of tris(pyridine)iridium(III) chloride.

The yield, at a purity of >99.9% by HPLC, was 5.83-6.05 g, corresponding to 89.0-92.3%.

$^1$H NMR (CDCl$_3$): [ppm]=see Example 2.

EXAMPLE 8 fac-Tris[2-(2-pyridinyl-κN)phenyl-κC]iridium(III)

Procedure similar to Example 6, except the iridium(III) chloride was replaced with 5.66 g (10 mmol) of tris(tetrahydrothiophene)iridium(III) chloride.

The yield, at a purity of >99.9% by HPLC, was 5.61-5.70 g, corresponding to 85.7-87.0%.

$^1$H NMR (CDCl$_3$): [ppm]=see Example 2.

What is claimed is:

1. A compound of the formula (I)

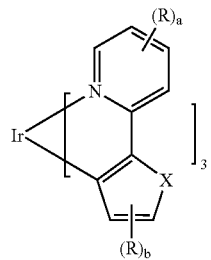

where
X is —CH=CH—, —CR=CH—, —CR=CR—, N—H, N—R$^1$, O, S or Se;
R is the same or different at each occurrence and is F, Cl, Br, NO$_2$, CN, a straight-chain or branched or cyclic alkyl or alkoxy group having from 1 to 20 carbon atoms, in each of which one or more nonadjacent CH$_2$ groups may be replaced by —O—, —S—, —NR$^1$, or —CONR$_2$—, and in each of which one or more hydrogen atoms may be replaced by F or an aryl or heteroaryl group having from 4 to 14 carbon atoms which may be substituted by one or more nonaromatic radicals R;
R$^1$ and R$^2$ are the same or different and are each H or an aliphatic or aromatic hydrocarbon radical having from 1 to 20 carbon atoms,
a is, 0 1, 2, 3or 4,
b is 0, 1 or 2,
whose purity (determined by means of HPLC) is more than 99%.

2. A compound of the formula (II)

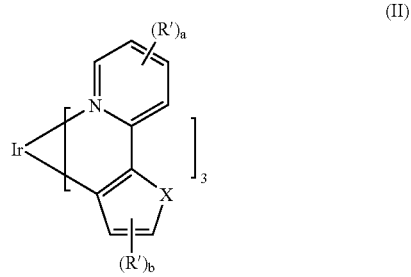

X is —CH=CH—, —CR=CH=, —CR=CR—, N—H, N—R$^1$, O, S or Se;
R' is the same or different at each occurrence and is F, a straight-chain or branched or cyclic alkyl group having from 1 to 20 carbon atoms, in which one or more hydrogen atoms may be replaced by F, or an aryl group having from 6 to 14 carbon atoms which may be substituted by one or more nonaromatic radicals R';
R$^1$ is in each case the same or different and is an aliphatic or aromatic hydrocarbon radical having from 1 to 20 carbon atoms,
a is 0, 1, 2, 3 or 4,
b is 0, 1 o 2,
whose purify (determined by means of HPLC) is more than 99%.

3. The compound according to claim 1, wherein a is 0 or 1 and b is 0 or 1.

4. The compound according to claim 1, wherein X is —CH=CH—, —CR=CH— or S.

5. The compound according to claim 3, wherein X is —CH=CH—, —CR=CH— or S.

6. The compound according to claim 2, wherein a is 0 or 1 and b is 0 or 1.

7. The compound according to claim 2, wherein X is —CH=CH—, —CR=CH— or S.

8. The compound according to claim 6, wherein X is —CH=CH—, —CR=CH— or S.

9. The compound as claimed in claim 1, wherein R is the same or different at each occurrence and is F, Cl, Br, NO$_2$, CN, a straight-chain or branched or cyclic alkyl or alkoxy group having from 1 to 20 carbon atoms, in each of which one or more nonadjacent CH$_2$ groups may be replaced by —O—, —S—, —NR$^1$,or —CONR$^2$—, and in each of which one or more hydrogen atoms may be replaced by F or an aryl or heteroaryl group having from 4 to 14 carbon atoms which may be substituted by one or more nonaromatic radicals R.

10. The compound as claimed in claim 1, wherein R is the same or different at each occurrence and is F, Cl, Br, NO$_2$, CN, a straight-chain or branched or cyclic alkyl or alkoxy group having from 1 to 20 carbon atoms, in each of which one or more nonadjacent CH$_2$ groups may be replaced by —O—, —S—, —NR$^1$, or —CONR$^2$—.

11. The compound as claimed in claim 1, wherein R is the same or different at each occurrence and is F, Cl, Br, NO$_2$, CN, a straight-chain or branched or cyclic alkyl or alkoxy group having from 1 to 20 carbon atoms.

12. The compound as claimed in claim 5, wherein R is the same or different at each occurrence and is F, Cl, Br, NO$_2$, CN, a straight-chain or branched or cyclic alkyl or alkoxy group having from 1 to 20 carbon atoms.

13. The compound as claimed in claim 2, wherein R' is the same or different at each occurrence and is F, a straight-chain or branched or cyclic alkyl group having from 1 to 20 carbon atoms, in which one or more hydrogen atoms may be replaced by F, or an aryl group having from 6 to 14 carbon atoms which may be substituted by one or more nonaromatic radicals R'.

14. The compound as claimed in claim 2, wherein R' is the same or different at each occurrence and is F, a straight-chain or branched or cyclic alkyl group having from 1 to 20 carbon atoms, in which one or more hydrogen atoms may be replaced by F, or an aryl group having from 6 to 14 carbon atoms.

15. The compound as claimed in claim 8, wherein R' is the same or different at each occurrence and is F, a straight-chain or branched or cyclic alkyl group having from 1 to 20 carbon atoms, in which one or more hydrogen atoms may be replaced by F, or an aryl group having from 6 to 14 carbon atoms.

* * * * *

UNITED STATES PATENT AND TRADEMARK OFFICE
CERTIFICATE OF CORRECTION

PATENT NO. : 7,423,151 B2
APPLICATION NO. : 11/483359
DATED : September 9, 2008
INVENTOR(S) : Philipp Stoessel et al.

It is certified that error appears in the above-identified patent and that said Letters Patent is hereby corrected as shown below:

In the Column 9, on line 19, "stirring for 16h. After cooling to room temperature, the", should read -- stirring for 60 h. After cooling to room temperature, the --.

Signed and Sealed this

Sixteenth Day of December, 2008

JON W. DUDAS
*Director of the United States Patent and Trademark Office*